(12) United States Patent
Van den Heuvel (10) Patent No.: US 10,512,775 B2
(45) Date of Patent: Dec. 24, 2019

(54) NOISE REDUCTION FOR IMPLANTABLE HEARING PROSTHESES

(71) Applicant: Cochlear Limited, Macquarie University, NSW (AU)

(72) Inventor: Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 281 days.

(21) Appl. No.: 15/690,948

(22) Filed: Aug. 30, 2017

(65) Prior Publication Data

US 2019/0060649 A1   Feb. 28, 2019

(51) Int. Cl.
*A61N 1/36* (2006.01)
*H04R 25/00* (2006.01)
*A61N 1/05* (2006.01)

(52) U.S. Cl.
CPC ....... *A61N 1/36038* (2017.08); *A61N 1/0541* (2013.01); *H04R 25/305* (2013.01); *H04R 25/505* (2013.01); *H04R 25/606* (2013.01); *H04R 2225/49* (2013.01); *H04R 2225/67* (2013.01)

(58) Field of Classification Search
None
See application file for complete search history.

(56) References Cited

U.S. PATENT DOCUMENTS

| 8,265,771 | B2 | 9/2012 | Donofrio et al. |
| 8,406,893 | B2 | 3/2013 | Krause et al. |
| 8,755,895 | B2* | 6/2014 | Litvak ............... A61N 1/37264 607/57 |
| 8,843,205 | B2* | 9/2014 | James ............... A61N 1/36036 607/57 |
| 9,162,069 | B2* | 10/2015 | Hemmert ........... A61N 1/36038 |

* cited by examiner

*Primary Examiner* — Brian T Gedeon
(74) *Attorney, Agent, or Firm* — Edell, Shapiro & Finnan, LLC (57) ABSTRACT

Presented herein are techniques for time interleaving the sampling of input signals with the delivery of stimulation signals to a recipient of an implantable electrically-stimulating hearing prosthesis. The input signals, which are received via one or more input channels and sampled by a sound processing unit, are susceptible to electrical feedback from the stimulation signals. As such, in accordance with embodiments presented herein, the sampling of the input signals by the sound processing unit, and the delivery of the stimulation signals to the recipient, are synchronized with one another so as to avoid stimulation-evoked electrical feedback within the input signals.

33 Claims, 9 Drawing Sheets

FIG. 7

NOISE REDUCTION FOR IMPLANTABLE HEARING PROSTHESES

BACKGROUND

Field of the Invention

The present invention relates generally to noise reduction for implantable hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to, for example, damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a totally implantable electrically-stimulating hearing prosthesis configured to be disposed in a recipient is provided. The totally implantable electrically-stimulating hearing prosthesis comprises: at least one input channel including an implantable sound sensor configured to convert received sound signals into electrical input signals; and a sound processing unit configured to sample the electrical input signals and to initiate generation of stimulation signals for delivery to the recipient via at least one output channel; wherein the sound processing unit is configured to synchronize sampling of the input signals and the delivery of the stimulation signals to the recipient so that the sampling is performed outside of a selected temporal proximity to the delivery of the stimulation signals.

In another aspect, a totally implantable electrically-stimulating hearing prosthesis configured to be disposed in a recipient is provided. The totally implantable electrically-stimulating hearing prosthesis comprises: at least one output channel terminating in an implantable electrode; at least one input channel comprising an implantable sound sensor configured to convert received sounds into input signals; and a sound processing unit configured to sample the electrical input signals and to initiate generation of stimulation signals for delivery to the recipient, wherein the sound processing unit executes a time interleaving scheme in which the sound processing unit samples the electrical input signals during a set of first time periods and in which the stimulation signals are delivered to the recipient during a set of second time periods, wherein the second time periods are interleaved with the first time periods in a successive and alternating pattern.

In another aspect, a method performed at an electrically-stimulating hearing prosthesis is provided. The method comprises: receiving sound signals via at least one input channel of the electrically-stimulating hearing prosthesis, wherein the at least one input channel includes at least one implantable sound sensor; at the least one implantable sound sensor, converting the detected sound signals into electrical input signals; sampling the electrical input signals at a sound processing unit to obtain input samples; delivering stimulation signals to the recipient via at least one output channel that includes at least one electrode; and implementing a time-division multiple access scheme in which the input signals are sampled by the sound processing unit during a set of first time periods and in which the stimulation signals are delivered to the recipient during a set of second time periods that are different from the first set of time periods.

BRIEF DESCRIPTION OF THE DRAWINGS

Embodiments of the present invention are described herein in conjunction with the accompanying drawings, in which.

DETAILED DESCRIPTION

Embodiments of the present invention are generally directed to techniques for time interleaving the sampling of input signals with the delivery of stimulation signals to a recipient of an implantable hearing prosthesis. The input signals, which are received via one or more input channels and sampled by a sound processing unit, are susceptible to electrical feedback from the stimulation signals. As such, in accordance with embodiments presented herein, the sampling of the input signals by the sound processing unit, and the delivery of the stimulation signals to the recipient, are synchronized with one another so as to avoid stimulation-evoked electrical feedback within the input signals. In certain embodiments, the hearing prosthesis implements a time-division multiple access (TDMA) technique in which the input signals are sampled only during a first set of time periods and the stimulation signals are only delivered to the recipient during a second set of time periods that are different from the first set of time periods.

There are a number of different types of implantable hearing prostheses in which embodiments of the present invention may be implemented. However, merely for ease of illustration, the techniques presented herein are primarily described with reference to one type of implantable hearing prosthesis, namely a totally/fully implantable cochlear implant. However, it is to be appreciated that the techniques presented herein may be used in other implantable hearing prostheses, such as auditory brainstem implants (stimulators), electro-acoustic hearing prostheses, vestibular implants, bimodal hearing prostheses, totally implantable acoustic hearing devices interconnected with another device which has an electrical output stimulator (e.g., vestibular implant, deep brain stimulator, etc.), etc.

Figure 1A:
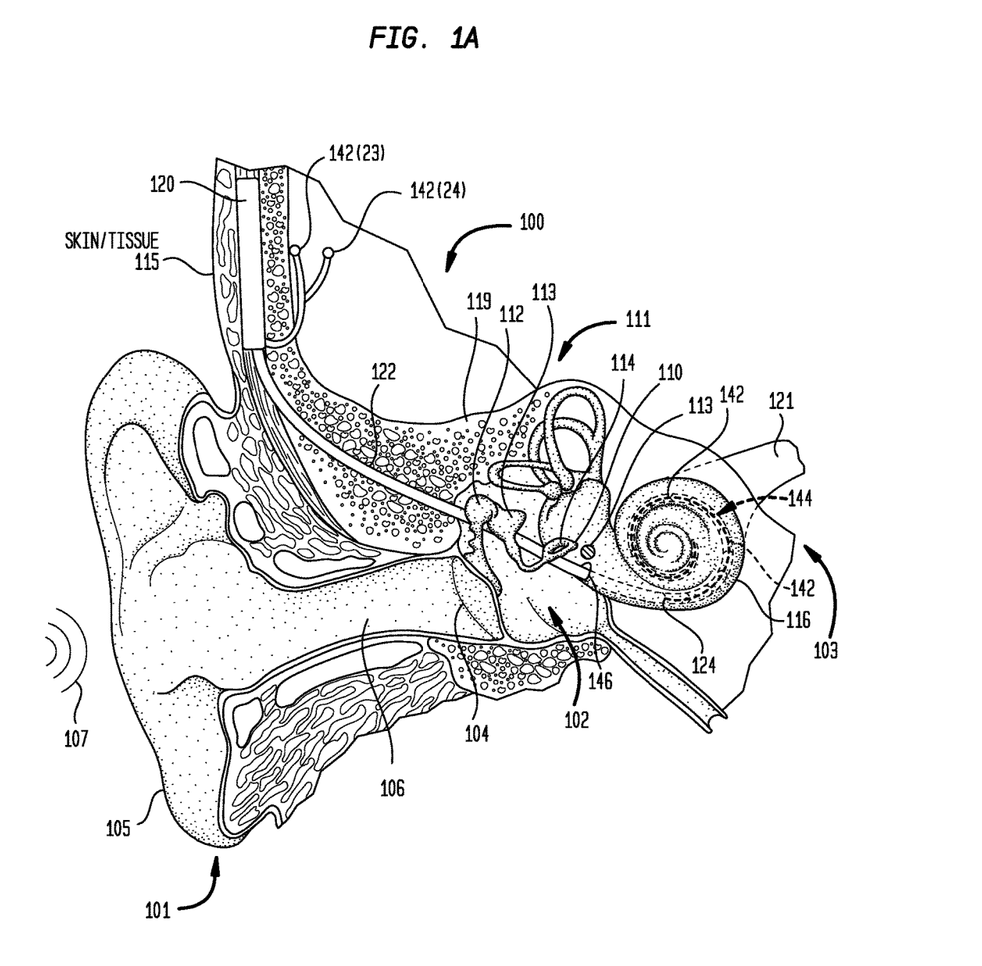
FIG. 1A is a schematic diagram illustrating a cochlear implant, in accordance with certain embodiments presented herein.
Figure 1B:
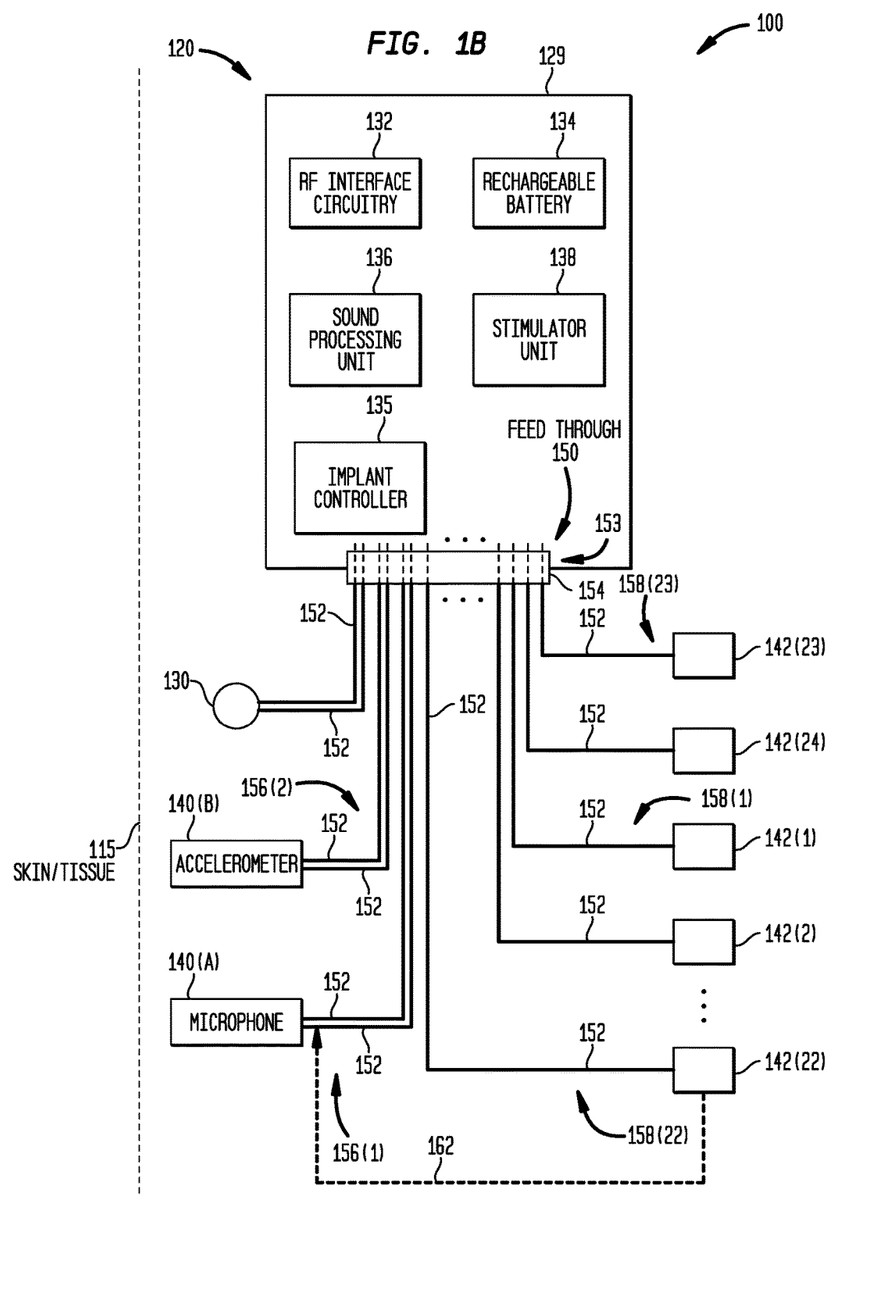
FIG. 1B is a block diagram of the cochlear implant of FIG. 1A.
Figure 1C:
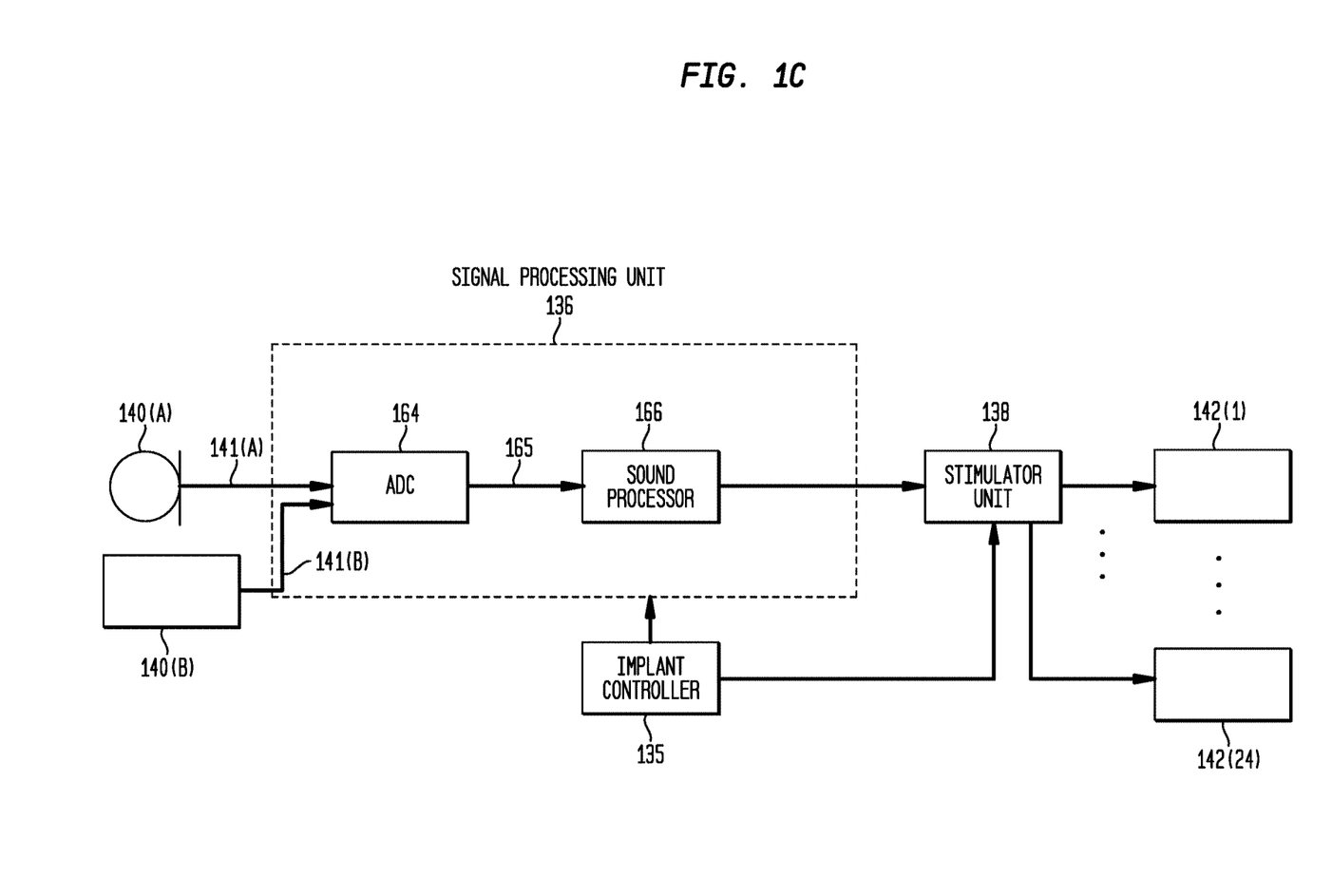
FIG. 1C is a functional block diagram illustrating further details of the cochlear implant of FIG. 1A.

FIG. 1A is schematic diagram of an exemplary totally/fully cochlear implant 100 configured to implement embodiments of the present invention, while FIGS. 1B and 1C are each block diagrams illustrating further details of the cochlear implant 100. For ease of description, FIGS. 1A, 1B, and 1C will be described together.

Shown in FIG. 1A is an outer ear 101, a middle ear 102 and an inner ear 103 of the recipient. In a fully functional human hearing anatomy, the outer ear 101 comprises an auricle 105 and an ear canal 106. Sound signals 107, sometimes referred to herein as acoustic sounds or sound waves, are collected by the auricle 105 and channeled into and through the ear canal 106. Disposed across the distal end of the ear canal 106 is a tympanic membrane 104 which vibrates in response to the sound signals (i.e., sound waves) 107. This vibration is coupled to the oval window or fenestra ovalis 110 through three bones of the middle ear 102, collectively referred to as the ossicular chain or ossicles 111 and comprising the malleus 112, the incus 113 and the stapes 114. The ossicles 111 of the middle ear 102 serve to filter and amplify the sound signals 107, causing oval window 110 to vibrate. Such vibration sets up waves of fluid motion within the cochlea 116 which, in turn, activates hair cells (not shown) that line the inside of the cochlea 116. Activation of these hair cells causes appropriate nerve impulses to be transferred through the spiral ganglion cells and the auditory nerve 118 to the brain (not shown), where they are perceived as sound.

As noted above, sensorineural hearing loss may be due to the absence or destruction of the cochlea hair cells, which transduce acoustic signals into nerve impulses. One treatment for such hearing loss is a cochlear implant, such as cochlear implant 100 shown in FIGS. 1A and 1B, which bypasses the cochlear hair cells and delivers stimulation (e.g., electrical stimulation) directly to the cochlea nerve cells.

In the illustrative embodiment of FIGS. 1A and 1B, the cochlear implant 100 is a "totally implantable" cochlear implant, meaning that all components of the cochlear implant are configured to be implanted under skin/tissue 115 of a recipient. Because all components of cochlear implant 100 are implantable, the cochlear implant operates, for at least a finite period of time, without the need of an external device. An external device can be used to, for example, charge an internal power source (battery) of the cochlear implant 100.

The cochlear implant 100 comprises an implant body or main module 120, a lead region 122, and an elongate intra-cochlear stimulating assembly 124. The implant body 120 comprises a hermetically sealed housing 129 in which radio frequency (RF) interface circuitry 132 (sometimes referred to as a transceiver unit), at least one rechargeable battery 134, an implant controller 135, a sound processing unit 136, and a stimulator unit 138 are disposed. The housing 129 operates as a protective barrier between the electrical components within the housing (e.g., in RF interface circuitry 132, battery 134, etc.) and the recipient's tissue and bodily fluid. For ease of illustration, electrical connections between the components within housing 129 have been omitted from FIG. 1B.

The implant body 120 also comprises one or more electrical components located outside (external to) the housing 129. The electrical components located outside the housing 129 include an internal/implantable coil 130, implantable sound sensors/transducers 140(A) and 140(B), and the elongate intra-cochlear stimulating assembly 124.

The RF interface circuitry 132 is connected to the implantable coil 130 and, generally, a magnet (not shown) is fixed relative to the implantable coil 130. Implantable coil 130 is typically a wire antenna coil comprised of multiple turns of electrically insulated single-strand or multi-strand platinum or gold wire. In general, the implantable coil 130 and the RF interface circuitry 132 enable the transfer of power and/or data from an external device to the cochlear implant 100. However, it is to be appreciated that various types of energy transfer, such as infrared (IR), electromagnetic, capacitive and inductive transfer, may be used to transfer power and/or data from an external device to a cochlear implant 100 and, as such, FIG. 1B illustrates only one example arrangement.

Elongate stimulating assembly 124 is configured to be at least partially implanted in cochlea 116 and extends through an opening in the cochlea 116 (e.g., cochleostomy 146, oval window 110, the round window 113, etc.). The stimulating assembly 124 has a proximal end connected to stimulator unit 138 via lead region 122 that extends through mastoid bone 119. Lead region 122 couples the stimulating assembly 124 to implant body 120 and, more particularly, to stimulator unit 138.

The stimulating assembly 124 includes a plurality of longitudinally spaced intra-cochlear electrical stimulating electrodes (electrodes) 142 that can be selectively used to deliver current to the cochlea 116. The stimulating electrodes 142 collectively form an intra-cochlear electrode array 144 that, in the example of FIG. 1B, comprises twenty-two (22) stimulating electrodes, labeled as electrodes 142(1)-142(22). Although FIG. 1B illustrates the use of twenty-two stimulating electrodes, is to be appreciated that different numbers, arrangements, etc., of intra-cochlear electrodes may be used in alternative embodiments.

Also shown in FIGS. 1A and 1B are two reference electrodes 142(23) and 142(24). The reference electrodes 142(23) and 142(24) are located outside of the cochlear 116 and can also be used to deliver current to the recipient. Since the reference electrodes 142(23) and 142(24) are located outside of the cochlea 116, the reference electrodes are sometimes referred to as extra-cochlear electrodes (ECEs).

As noted above, the cochlear implant 100 comprises two implantable sound sensors 140(A) and 140(B). In the illustrative embodiment of FIG. 1B, the implantable sound sensor 140(A) is a sensor/transducer that is primarily configured to detect/receive external acoustic sounds (e.g., an implantable microphone), while the implantable sound sensor 140(B) is a sound sensor that is primarily configured to detect/receive internal body noises (e.g., another implantable microphone or an accelerometer which is configured to be more sensitive to body noises than it is to external acoustic sound signals). As used herein, body noises (BNs) are undesirable sounds induced by the body that are propagated primarily as vibration, such as breathing, scratching, rubbing, noises associated with the movement of the head, chewing, own voice, etc. For ease of description, embodiments presented herein will be primarily described with reference to the use of an implantable microphone 140(A) as the first sound sensor and an accelerometer 140(B) as the second sound sensor. However, it is to be appreciated that these specific implementations are non-limiting and that embodiments of the present invention may be used with a number of other different types of implantable sensors. For example, an implantable electrically-stimulating hearing prosthesis may also include other types of sensors, such as a telecoil, sensors for picking up nerve signals (e.g., an electroencephalogram (EEG)), etc. As such, the microphone 140(A) and the accelerometer 140(B) are merely illustrative of a number of different types of implantable sensors that may be affected by electrical feedback from output (stimulation) channels, as described elsewhere herein.

In operation, the microphone 140(A) and the accelerometer 140(B) detect sound signals (e.g., external acoustic sounds and/or body noises) and convert the detected sound signals into analog electrical signals. The electrical signals generated by the microphone 140(A) and the accelerometer 140(B) are received by the sound processing unit 136, which is configured to sample the electrical signals to generate "input samples." The input samples represent the sound signals at a given time point. The sound processing unit 136 is further configured to execute signal processing and coding to convert the input samples into processed signals that represent the detected sound signals. The sound processing unit 136 is then configured to initiate generation of stimulation signals for delivery to the recipient via at least one output channel by providing the processed signals to the stimulator unit 138. The stimulator unit 138 is configured to utilize the processed signals to generate electrical stimulation signals that are delivered to the recipient's cochlea via one or more of the intra-cochlear stimulating electrodes 142(1)-142(22) implanted in the recipient's cochlea 116. In this way, cochlear implant 100 stimulates the recipient's auditory nerve cells, bypassing absent or defective hair cells that normally transduce acoustic vibrations into neural activity.

As noted above, cochlear implant 100 includes one or more electrical components positioned in the hermetic housing 129, as well as one or more electrical components located outside the hermetic housing 129. There is a need to enable electrical connections between various components outside of the hermetic housing 129 with various components within the housing 129. As such, the cochlear implant 100 includes a hermetic feedthrough 150 that provides a physical electrical connection that is used to transfer signals to/from the electrical components outside of the hermetic housing 129 to/from the electrical components within the hermetic housing 129. In FIG. 1B, conductors 152 extend from the hermetic feedthrough 150 to internal coil 130, microphone 140(A), accelerometer 140(B), reference electrode 142(23), reference electrode 142(24), and to each of the intra-cochlear stimulating electrodes 142(1)-142(22). For ease of illustration, FIGS. 1B and 1C illustrate only a subset of the intra-cochlear stimulating electrodes 142(1)-142(22) and, accordingly, only a subset of the conductors 152 extending to the intra-cochlear stimulating electrodes 142(1)-142(22).

The term "input channel" is used herein to refer to the combination of a sound sensor and an associated conductor that connects the sound sensor to another component (e.g., feedthrough wire). In the embodiments of FIGS. 1A-1C, the microphone 140(A) and the accelerometer 140(B) are sound sensors that are each associated with one or more conductors 152. As such, cochlear implant 100 includes two input channels, referred to as input channel 156(1) and input channel 156(2). Input channel 156(1) includes the microphone 140(A) and the associated conductor(s) 152 and input channel 156(2) includes the accelerometer 140(B) and the associated conductor(s) 152. As noted above, an electrically-stimulating hearing prosthesis in accordance with embodiments presented herein may comprise additional or alternative input channels that include, for example, telecoils, sensors for picking up nerve signals, etc. As such, the input channels 156(1) and 156(2) are merely illustrative of a number of different types of implantable channels may be affected by electrical feedback from output channels, as described elsewhere herein.

The term "output channel" is used herein to refer to the combination of an electrode and an associated conductor that connects the electrode to another component (e.g., feedthrough wire). In the embodiments of FIGS. 1A and 1B, the intra-cochlear stimulating electrodes 142(1)-142(22), reference electrode 142(23), and reference electrode 142(24) are each associated with one or more conductors 152. As such, cochlear implant 100 includes twenty-four (24) output channels 158(1)-158(24), where each output channel is formed by a corresponding electrode 142(1)-142(24) and one or more associated conductors 152.

Prior to implantation, the housing 129, the internal coil 130, the feedthrough 150, and at least a portion of the conductors 152 in proximity to the feedthrough 150 may be overmolded/encapsulated with a silicone elastomer to create a uniform compliant surface suitable for implantation. This encapsulation, which has been omitted from FIGS. 1A-1C for ease of illustration, generally isolates the internal coil 130 and the conductors 152 in proximity to the feedthrough 150 from each other and from the implanted environment. That is, the encapsulation is generally resistant to the ingress of bodily fluid and has material properties that electrically isolate each of the conductors 152 and the internal coil 130.

A hermetic feedthrough, such as hermetic feedthrough 150, may be one of the most complex mechanical structures in an implantable medical device and are difficult to form properly. Hermetic feedthrough 150 includes an insulator 154 (e.g., formed from ceramic) and one or more conductors 153 (e.g., formed from platinum) that extend through the insulator. Due to the requirements of the manufacturing process, the conductors 153 extending through the insulator 154 are uninsulated and can comprise, or be joined to, the conductors 152. Therefore, at the outer surface of the hermetic feedthrough 150, only the applied encapsulation isolates the conductors 152 or 153.

As described in detail above, the cochlear implant 100 includes both implanted sound sensors (e.g., microphone 140(A) and accelerometer 140(B)) as well as implanted stimulation components (e.g., intra-cochlear electrodes 142(1)-142(22) and reference electrodes 142(23)-142(24)). The sound sensors are used to capture input sound signals (e.g., acoustic sounds, body noises, etc.), which in turn are used by the cochlear implant 100 to generate stimulation signals for delivery to the recipient. That is, the cochlear implant 100 is a totally implantable device that is configured to: (1) detect/receive sounds from within the recipient, (2) process the sounds, and (3) generate stimulation signals for delivery to the recipient to evoke perception of the sound signals. As such, the use of the implantable sound sensors 140(A) and 140(B) provide the recipient with the ability to have a truly "invisible" prosthesis (i.e., since there are no external components, the prosthesis is invisible to others).

Although the use of the implanted sound sensors 140(A) and 140(B) facilitates the totally implantable nature of the cochlear implant 200, it has been discovered that there is a potential for the creation of an electrical feedback path between an output channel and an input channel, where "electrical feedback" (i.e., a portion of the stimulation signals) will appear in the input channel. For example, an electrical feedback path may be created between the stimulation components themselves (e.g., electrodes 142(1)-142(24)) and the sound sensors themselves (e.g., microphone 140(A) and accelerometer 140(B)) via the recipient's tissue/fluid. In other examples, fluid ingress (leakage) into the encapsulation at the feedthrough 150 can lead to the creation of conductive pathways between the conductors 152/153 connected to the sound sensors and the conductors 152/153 connected to the electrodes 142(1)-142(24 (i.e., the silicone encapsulation provides a high impedance insulation between the wires, but over time body fluids can leak under the silicone on the outside of the feedthrough and create a slightly conduct path between the stimulator wires and the microphone/accelerometer wires). In general, stimulation signals at the output channels have magnitudes that are significantly larger than the magnitudes of input signals on the input channels. That is, the output channels carry high voltage stimulation signals (e.g., up to the order of 10Volts) while the input channels carry low voltage input signals (e.g., on the order of several millivolts). Due to this voltage difference, the electrical feedback (i.e., a portion of the high voltage stimulation signals that pass through an electrical feedback path to one or more input channels) will cause electrical interference within the sound samples obtained at the input channels. In certain embodiments, this electrical interference may be perceived by the recipient as audible noise. In FIG. 1B, the presence of any number of electrical feedback paths between output channel 158(22) and input channel 156(1) is represented by arrow 162. Arrow 162 is illustrative and, as noted, there is a possibility that electrical feedback paths could be created between any of the twenty-four output channels 158(1)-158(24) and either of the input channels 156(1) and 156(2).

Prior art devices have attempted to improve the signal delivered to the recipient by, for example, subtracting body noise as measured by an accelerometer from the sounds detected by the implanted microphone. However, in such devices, the problem of unwanted noise still persists, particularly in the presence of electrical feedback, despite attempts to improve the adaptive noise reduction with better signal processing algorithms.

The present inventor has discovered that at least some recipients may have an improved hearing experience by specifically controlling, in a recipient-specific manner, the timing of the input sampling with respect to that of the delivery of the output stimulation. The techniques presented herein mitigate the effects of unexpected electrical feedback paths that may appear, for example, due to manufacturing variability in the feedthrough encapsulation. Certain recipients may have unique perceptual capacities so as to tolerate a modified timing relationship in a way that improves rather than detracts from the overall experience.

FIG. 1C is a functional block diagram illustrating further details of the sound processing unit 136, as well as inter-operation of the sound processing unit 136 with the implant controller 135, in accordance with embodiments presented herein. As shown, the sound processing unit 136 comprises an Analog-to-Digital converter (ADC) 164 and a sound processor 166 (e.g., digital sound processor). As noted above, the microphone 140(1) and the accelerometer 140(B) detect sound signals (e.g., external acoustic sounds and/or body noises) and convert the detected sound into analog input signals, shown in FIG. 1C as input signals 141(A) and 141(B), which are provided to the ADC 164. The ADC 164 is configured to take samples of (i.e., to sample) the analog input signals 141(A) and 141(B) and, accordingly, generate input samples 165 (i.e., a digitized output that represents the input signals 141(A) and 141(B) received from the microphone 140(1) and/or the accelerometer 140(B)) that are provided to the sound processor 166.

In conventional arrangements, an ADC samples the analog input signals from the sound sensors at a rate that is sufficient to ensure that all portions of the original sound signals are represented in the input samples. In addition, in conventional arrangements, the sampling of the analog input signals is independent from the delivery of the stimulation signals to the recipient. As noted above, electrical feedback paths may exist between output channels and input channel and, in certain examples, it may not be possible to eliminate these electrical feedback paths. As such, in conventional arrangements, when electrical feedback paths are present, it is possible that portions of the stimulation signals delivered to the recipient will be appear in the input samples obtained by the ADC (i.e., a portion of the stimulation signals pass through the electrical feedback path and are captured with the actual sound in the input samples). As noted, the presence of portions of the stimulation signals, referred to herein as stimulation-evoked electrical feedback or stimulation noise, may be perceived by the recipient as audible noise.

The stimulation-evoked electrical feedback may be particularly problematic given that the delivered stimulation and the input signals are located in overlapping frequency bands.

As described further below, embodiments presented herein address the above problems by synchronizing the timing of the ADC sampling with the timing of the delivery of stimulation signals to the recipient so that the input sampling is substantially restricted to time periods during which no stimulation signals are delivered to the recipient. That is, presented herein are techniques that use a time interleaving technique to reduce or substantially eliminate the effect of the stimulation-evoked electrical feedback on the input samples obtained at the input channels. In general, the ADC sampling is performed either between delivery of individual stimulation signals (electrical pulses), or between delivery of groups of stimulation signals, in order to avoid sampling the stimulation-evoked electrical feedback.

More specifically, in the embodiment of FIGS. 1A-1C, the sound processing unit 136, and more particularly the ADC 164, is configured (e.g., by the implant controller 135) to sample the analog input signals 141(A) and/or 141(2) only during a set of first time periods. In addition, the sound processing unit 136, and more particularly the sound processor 166, is configured to initiate generation of stimulation signals for delivery to the recipient only during a set of second time periods (i.e., the sound processor 166 provides processed signals to the stimulator unit 138, which generates and delivers stimulation signals to the recipient only during the set of second time periods). The first time periods during which the analog input signals are sampled are referred to herein as "sampling periods," while the second time periods during which stimulation signals are delivered to the recipient are referred to herein as "stimulation periods."

In other words, in accordance with embodiments presented herein, the cochlear implant 100 implements a time-division multiple access (TDMA) technique in which the input signals are sampled only during sampling time periods, while the stimulation signals are only delivered to the recipient during the stimulation time periods, which are different from the sampling time periods. As a result, the sampling of the input signals only occurs outside of a selected temporal proximity to the delivery of a stimulation signal (i.e., outside of a selected time frame preceding and/or following delivery of the stimulation signal) that is sufficient to ensure that that the stimulation-evoked electrical feedback does not affect the input samples, thereby largely avoiding stimulation-evoked electrical feedback resulting from the electrical feedback path(s) between the output channels 158(1)-158(24) and the input channels 156(1)-156(2).

Figure 2A:
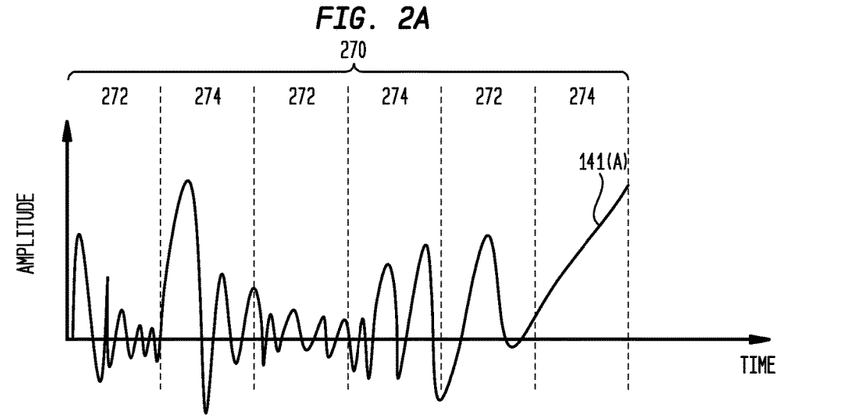
FIG. 2A is a graph illustrating an input signal received during a time window, in accordance with certain embodiments presented herein.
Figure 2B:
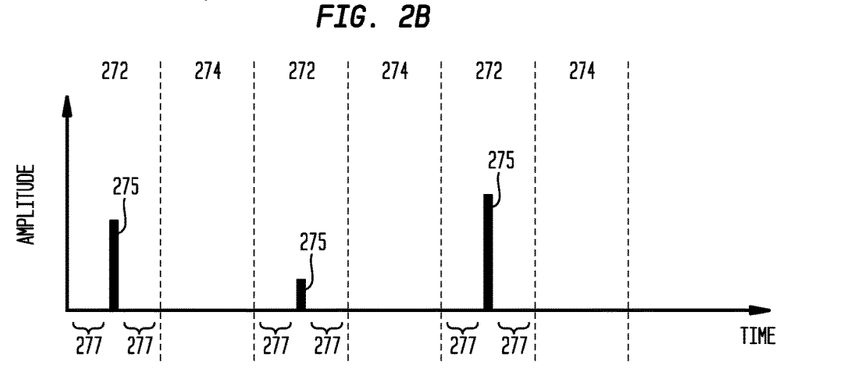
FIG. 2B is a graph illustrating sampling of the input signal of FIG. 2A, in accordance with a sampling and stimulation interleaving technique presented herein.
Figure 2C:
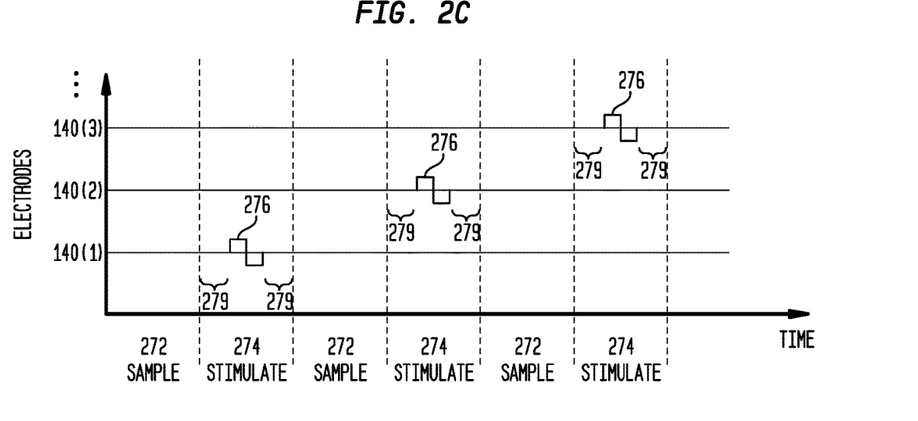
FIG. 2C is a graph illustrating delivery of stimulation signals to a recipient based on samples of the input signal of FIG. 2A.

FIG. 2A is a graph illustrating an analog signal received during a time window 270, while FIG. 2B is a graph illustrating restricted sampling of the analog signal of FIG. 2A during the time window 270, in accordance with embodiments presented herein. FIG. 2C is a graph illustrating the delivery of stimulation signals to a recipient during the time window 270. For ease of illustration, FIGS. 2A-2C will be described with reference to the arrangement of FIGS. 1A-1C, namely with reference to analog input signal 141(A) received from microphone 140(A) during the time window 270. For purposes of illustration, it is assumed that no sound signals are received by accelerometer 140(B) during the time window 270. However, in practice, during any given time window, sound signals may be received by either or both of the microphone 140(A) and the accelerometer 140(B) and may be simultaneously sampled and processed in a similar manner.

FIG. 2A illustrates the amplitude of the input signal 141(A) during the time window 270. As shown in FIGS. 2A-2C, the time window 270 is divided into first and second sets of time periods/slots. The first set of time periods is formed by the sampling periods 272, while the second set of time periods is formed by the stimulation periods 274. As shown in FIG. 2B, the input signal 141(A) is sampled only during the sampling periods 272 while, as shown in FIG. 2C, stimulation signals (current signals) 276 are delivered to the recipient only during each of the stimulation periods 274. The sampling periods 272 and the stimulation periods 274 comprise successive and alternating time periods, each having a selected time length. That is, the stimulation periods 274 are interleaved with the sampling periods 272.

FIGS. 2A-2C also illustrate that the sampling periods 272 and the stimulation periods 274 have approximately the same time length and that the time length is fixed (constant) across the time window 270. FIG. 2B illustrates that one (1) sample 275 is obtained during each of the sampling periods 272, for a total of three (3) samples by ADC 164 during time window 270. FIG. 2C illustrates that one (1) stimulation signal 276 is delivered via one or more electrodes during each of the stimulation periods 274, for a total of three (3) stimulation signals during time window 270. Merely for ease of illustration, FIG. 2C illustrates that the stimulation signals 276 are biphasic pulses that are delivered via electrode 140(1) during the first stimulation delivery period 274, via electrode 140(2) during the second stimulation delivery period 274, and via electrode 140(3) during the third stimulation delivery period 274. In other embodiments, the stimulation signals 276 may have other firms and may be delivered via any of the implanted electrodes, such as any of the intra-cochlear electrodes 140(1)-140(22).

As shown in FIGS. 2A-2C, the input signal 141(A) is only sampled for a portion (subset) of the sampling periods 272. Similar, the stimulation signals 276 are only delivered for a portion of the stimulation periods 274. As a result, the sampling periods 272 and the stimulation periods 274 each include vacant or unoccupied portions, primarily at the beginning and/or end of the corresponding periods. This is shown as unoccupied portions 277 at the beginning and end of each sampling period 272 and unoccupied portions 279 at the beginning and end of each stimulation period 274. The unoccupied portions 277 and 279 are provided as a buffer to prevent overlap in the stimulation and sampling (i.e., to ensure that the sampling is only performed outside of a selected time frame preceding and/or following delivery of the stimulation signal).

In summary, in the embodiments of FIGS. 2A-2C the cochlear implant 100 implements a time interleaving scheme to alternatively sample the input signals and to stimulate the recipient in separate time periods. The sampling of the input signal 141(A) by the ADC 164 is restricted so as to only occur during time periods in which no electrical stimulation is delivered to the recipient.

It is to be appreciated that the specific arrangement of the sampling periods 272 and the stimulation periods 274 shown in FIGS. 2A-2C are illustrative and that the techniques presented herein may be implemented in a number of other manners. FIGS. 3A-3C, 4A-4C, and 5A-5C each illustrate different implementations for the techniques presented herein. FIGS. 3A-3C, 4A-4C, and 5A-5C are each described with reference to analog input signal 141(A) received from microphone 140(A) during a time period, while no input signals are received by accelerometer 140(B).

Figure 3A:
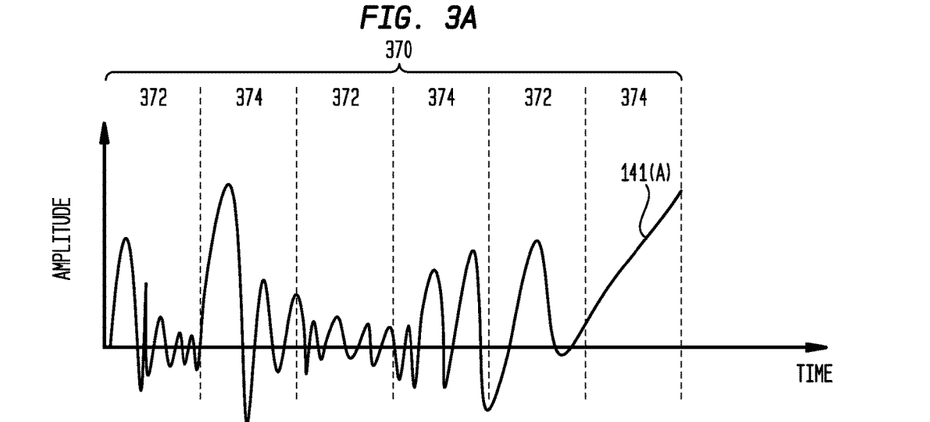
FIG. 3A is a graph illustrating an input signal received during a time window, in accordance with certain embodiments presented herein.
Figure 3B:
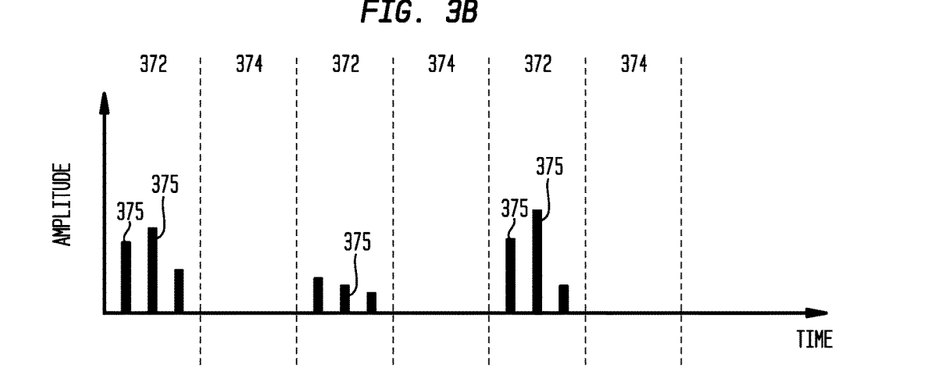
FIG. 3B is a graph illustrating sampling of the input signal of FIG. 3A, in accordance with a sampling and stimulation interleaving technique presented herein.
Figure 3C:
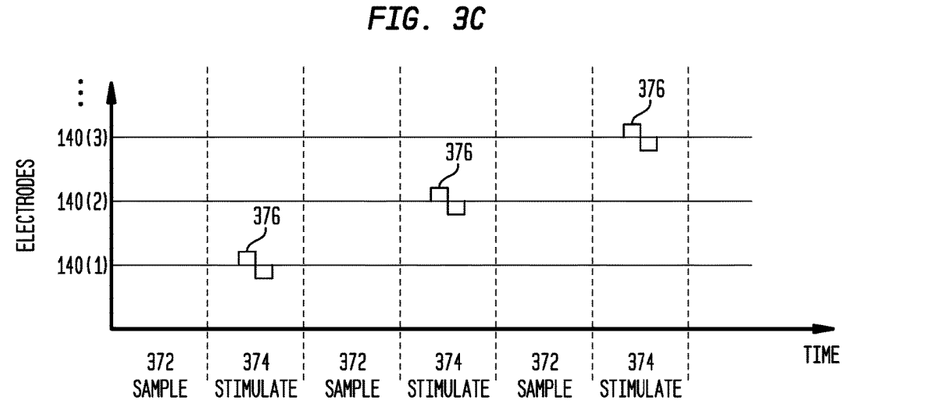
FIG. 3C is a graph illustrating delivery of stimulation signals to a recipient based on samples of the input signal of FIG. 3A.

Referring first to FIGS. 3A-3C, FIG. 3A is a graph illustrating the amplitude of the analog signal 140(1) during a time window 370. As shown in FIGS. 3A-3C, the time window 370 is divided into first and second sets of time periods/slots. The first set of time periods is formed by the sampling periods 372, while the second set of time periods is formed by the stimulation periods 374.

As shown in FIG. 3B, the input signal 141(A) is sampled by the ADC 164 only during each of the sampling periods 372 while, as shown in FIG. 3C, stimulation signals 376 are delivered to the recipient only during each of the stimulation periods 374. The sampling periods 372 and the stimulation periods 374 collectively comprise a pattern of successive and alternating time periods, each having a selected time length. In other words, in FIGS. 3A-3C, the stimulation periods 374 are interleaved with the sampling periods 372 (i.e., cochlear implant 100 implements a time interleaving scheme).

FIGS. 3A-3C illustrate that the sampling periods 372 and the stimulation periods 374 have approximately the same time length and that the time length is fixed (constant) across the time window 370. FIG. 3B illustrates that three (3) samples 375 are obtained during each of the sampling periods 372, for a total of nine (9) samples at ADC 164 during time window 370. FIG. 3C illustrates that one (1) stimulation signal 376 is delivered during each of the stimulation periods 374, for a total of three (3) stimulation signals during time window 370. In other words, FIGS. 3B and 3C illustrate that, in these embodiments, multiple input signal samples 375 are obtained between each of the stimulating pulses 376. Merely for ease of illustration, FIG. 3C illustrates that the stimulation signals 376 are biphasic pulses delivered via electrode 140(1) during the first stimulation delivery period 374, via electrode 140(2) during the second stimulation delivery period 374, and via electrode 140(3) during the third stimulation period 374.

Figure 4A:
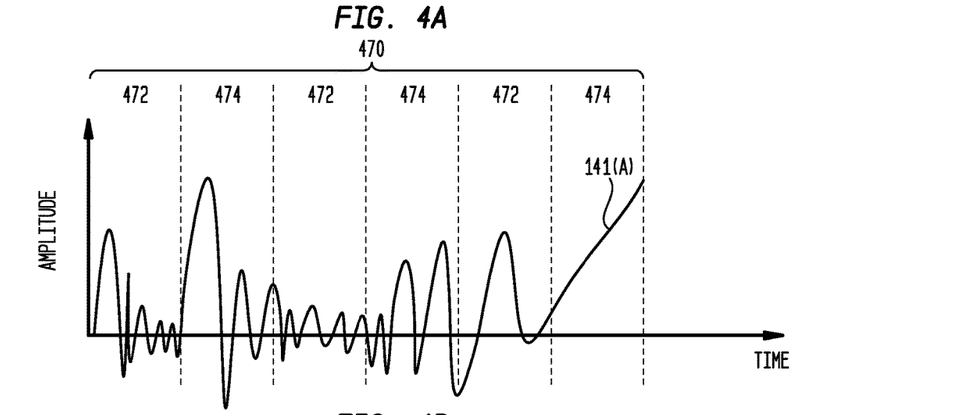
FIG. 4A is a graph illustrating an input signal received during a time window, in accordance with certain embodiments presented herein.
Figure 4B:
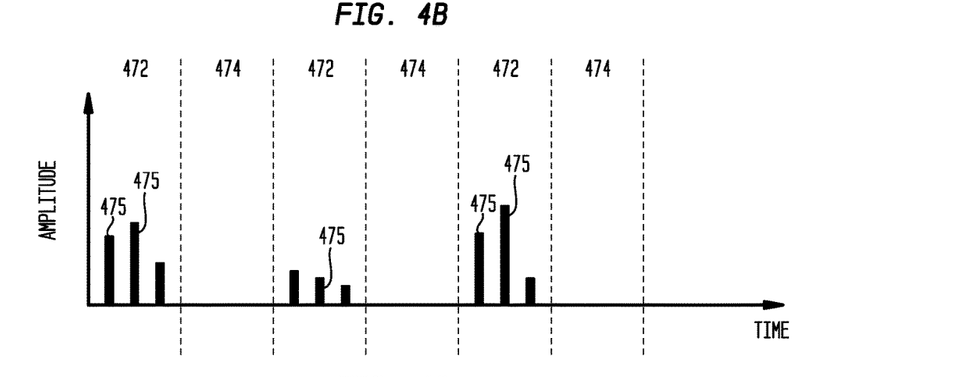
FIG. 4B is a graph illustrating sampling of the input signal of FIG. 4A, in accordance with a sampling and stimulation interleaving technique presented herein.
Figure 4C:
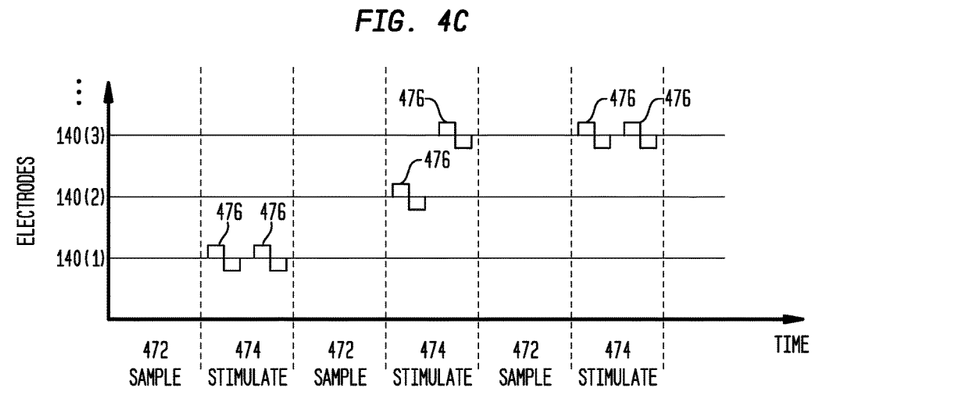
FIG. 4C is a graph illustrating delivery of stimulation signals to a recipient based on samples of the input signal of FIG. 4A.

Referring next to FIGS. 4A-4C, FIG. 4A is a graph illustrating the amplitude of the analog signal 140(1) during a time window 470. As shown in FIGS. 4A-4C, the time window 470 is divided into first and second sets of time periods/slots. The first set of time periods is formed by the sampling periods 472, while the second set of time periods is formed by the stimulation periods 474.

As shown in FIG. 4B, the input signal 141(A) is sampled by the ADC 164 only during each of the sampling periods 472 while, as shown in FIG. 4C, stimulation signals 476 are delivered to the recipient only during each of the stimulation periods 474. The sampling periods 472 and the stimulation periods 474 collectively comprise a pattern of successive and alternating time periods, each having a selected time length. In other words, in FIGS. 4A-4C, the stimulation periods 474 are interleaved with the sampling periods 472 (i.e., cochlear implant 100 implements a time interleaving scheme).

FIGS. 4A-4C illustrate that the sampling periods 472 and the stimulation periods 474 have approximately the same time length and that the time length is fixed (constant) across the time window 470. FIG. 4B illustrates that three (3) samples 475 are obtained during each of the sampling periods 472, for a total of nine (9) samples at ADC 164 during time window 470. FIG. 4C illustrates that two (2) stimulation signals 476 are delivered during each of the stimulation periods 474, for a total of six (6) stimulation signals during time window 470. In other words, FIGS. 4B and 4C illustrate that, in these embodiments, multiple input signal samples 475 are obtained between groups of stimulating pulses 476.

Merely for ease of illustration, FIG. 4C illustrates that the stimulation signals 476 are biphasic pulses delivered via electrodes 140(1), 140(2), and 140(3). More specifically, during the first stimulation delivery period 474, both of the stimulation signals 476 are delivered via electrode 140(1). During the second stimulation delivery period 474, the first stimulation signal 476 is delivered via electrode 140(2), while the second stimulation signal 476 is delivered via electrode 140(3). During the third stimulation delivery period 474, both of the stimulation signals 476 are delivered via electrode 140(3). As such, FIG. 4C illustrates that, in a given stimulation delivery period 474, the multiple stimulation signals may be delivered via one or more electrodes. Within a given stimulation delivery period 474, the multiple stimulation signals may also be delivered via the one or more electrodes sequentially or simultaneously across multiple electrodes.

Figure 5A:
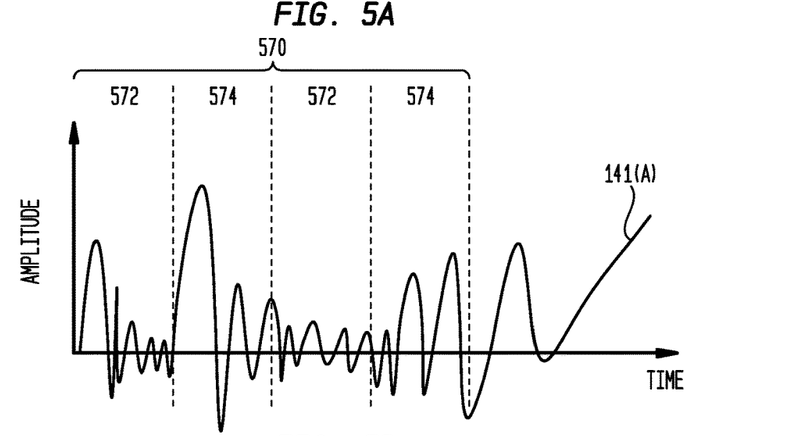
FIG. 5A is a graph illustrating an input signal received during a time window, in accordance with certain embodiments presented herein.
Figure 5B:
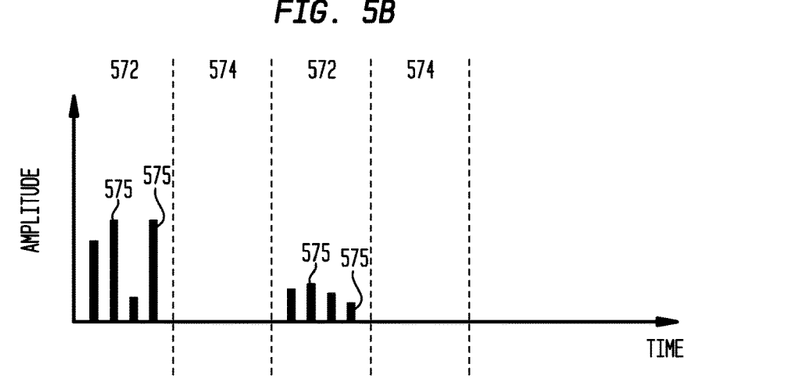
FIG. 5B is a graph illustrating sampling of the input signal of FIG. 5A, in accordance with a sampling and stimulation interleaving technique presented herein.
Figure 5C:
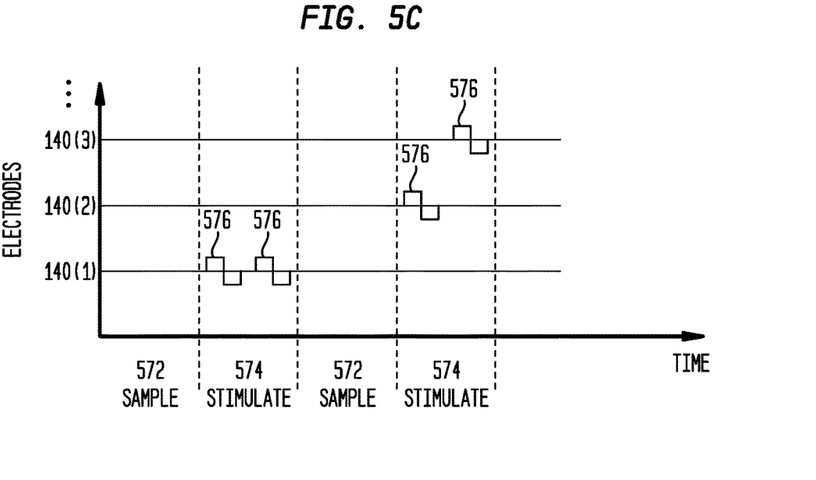
FIG. 5C is a graph illustrating delivery of stimulation signals to a recipient based on samples of the input signal of FIG. 5A.

Referring next to FIGS. 5A-5C, FIG. 5A is a graph illustrating the amplitude of the analog signal 140(1) during a time window 570. As shown in FIGS. 5A-5C, the time window 570 is divided into first and second sets of time periods/slots. The first set of time periods is formed by the sampling periods 572, while the second set of time periods is formed by the stimulation periods 574.

As shown in FIG. 5B, the input signal 141(A) is sampled by the ADC 164 only during each of the sampling periods 572 while, as shown in FIG. 5C, stimulation signals 576 are delivered to the recipient only during each of the stimulation periods 574. The sampling periods 572 and the stimulation periods 574 collectively comprise a pattern of successive and alternating time periods, each having a selected time length. In other words, in FIGS. 5A-5C, the stimulation periods 574 are interleaved with the sampling periods 572 (i.e., cochlear implant 100 implements a time interleaving scheme).

FIGS. 5A-5C also illustrate that the sampling periods 572 each have a fixed time length that is greater than the fixed time length of the stimulation periods 574. In addition, FIG. 5B illustrates that four (4) samples 575 are obtained during each of the sampling periods 572, for a total of eight (8) samples at ADC 164 during time window 570. FIG. 5C illustrates that two (2) stimulation signals 576 are delivered during each of the stimulation periods 574, for a total of four (4) stimulation signals during time window 570.

As such, FIGS. 5B and 5C illustrate that, in certain embodiments: (1) the sampling periods 572 and the stimulation periods 574 may have different time lengths; (2) multiple samples may be obtained during a single sampling period 572, and (3) multiple stimulation signals may be delivered via one or more electrodes during a single stimulation delivery period 574.

Figure 6:
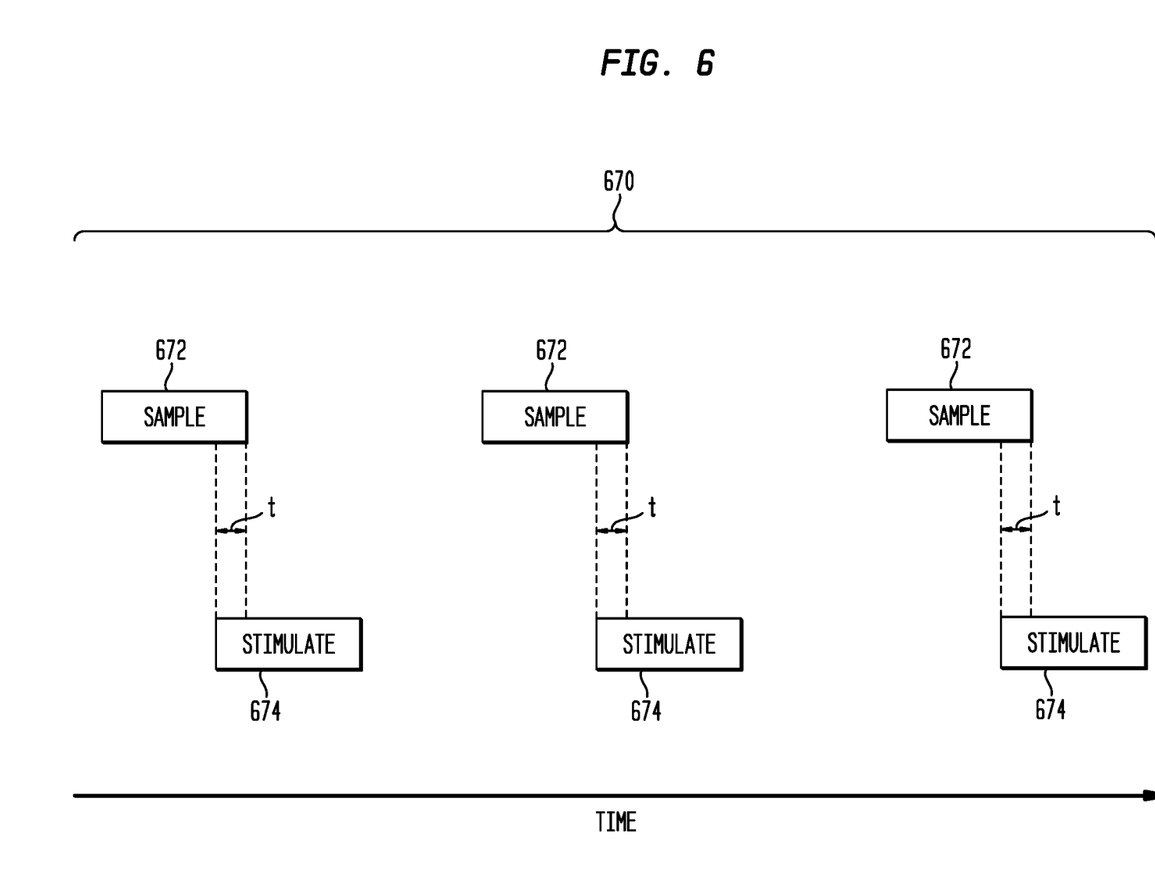
FIG. 6 is a schematic diagram illustrating overlapping sampling and stimulation periods, in accordance with certain embodiments presented herein.

FIGS. 2A-2C, 3A-3C, 4A-4C, and 5A-5C generally illustrate non-overlapping sampling periods and stimulation periods. However, it is to be appreciated that sampling periods and stimulation periods in accordance with embodiments presented herein are not necessarily mutually exclusive, but instead may overlap with one another in different manners, so long as the sampling of the input signals only occurs outside of a selected temporal proximity to the delivery of a stimulation signal (i.e., outside of a selected time frame preceding and/or following delivery of the stimulation signal) that is sufficient to ensure that that stimulation-evoked electrical feedback does not affect the input samples FIG. 6 is a schematic diagram illustrating one example arrangement in which sampling periods 672 and stimulation periods 674 overlap with one another during a time window 670. In these examples, each stimulation delivery period 674 begins before the previous sampling period 672 ends (i.e., the beginning of each stimulation delivery period 674 overlaps with the end of the preceding sampling period 672 by a time (t)). Although the sampling periods 672 and stimulation periods 674 overlap with one another, in these embodiments, the timing of the input sampling and the stimulation signal delivery are still synchronizes with one another such that electrical feedback from the stimulation signals is largely absence from the sampling. That is, even with overlapping sampling periods 672 and stimulation periods 674, the sampling of the input signals occurs only outside of a selected temporal proximity to the delivery of a stimulation signal (i.e., outside of a selected time frame preceding and/or following delivery of the stimulation signal) that is sufficient to ensure that that stimulation-evoked electrical feedback does not affect the input samples.

As described in detail above, in an electrically-stimulating hearing prosthesis in accordance with embodiments presented herein, sampling of the input signal(s) is interleaved with delivery of stimulation signals to a recipient of the electrically-stimulating hearing prosthesis. The result of this arrangement is that embodiments presented herein intentionally introduce gaps/breaks in the stream of input samples. As a result of the introduced gaps, incoming sound information is intentionally omitted/ignored (i.e., the interleaving creates "gaps" in the sound data that is available for use by the sound processor). In certain embodiments presented herein, an electrically-stimulating hearing prosthesis may be configured to compensate for the missing incoming sound information.

For example, referring to the arrangement of FIGS. 1A-1C, in one embodiment the sound processor 166 may be configured to interpolate between input samples to estimate the missing incoming sound information (i.e., use the previous two, three, etc. samples to estimate the next subsequent input sample that is omitted/missing). The interpolated data may be used along with the sound data obtained from the input samples to generate stimulation signals for delivery to the recipient. In another embodiment, the sound processor 166 may be configured to duplicate/repeat the one or more previous samples or set of samples in order to complete the gaps in the sound data (i.e., duplicate one or more input samples in place of the missing incoming sound information).

As detailed above, in accordance with embodiments presented herein, the interleaving parameters (i.e., the various attributes of the interleaved sampling and stimulation, such as the time length of the sampling periods, time length of the stimulation periods, the number of samples taken within a sampling period, the number of stimulation signals delivered within a stimulation period, etc.) may vary. In certain embodiments, the interleaving parameters are recipient-specific and set/fixed during a fitting session (e.g., set appropriate parameters that optimize sound perception for the recipient during a clinical fitting session, a remote fitting session, a recipient-directed fitting session, etc.).

It is also to be appreciated that the recipient-specific interleaving parameters can, in certain embodiments, be changed over the life of the cochlear implant 100. These interleaving parameters change may be induced, for example, in response to changes in the electrical feedback paths that are present (e.g., increased fluid ingress at the feedthrough 150, etc.), in response to changes in the recipient's hearing, etc. These changes can be effectuated during a subsequent fitting session or automatically by the cochlear implant 100, as described further below.

In further embodiments, the interleaving parameters may be adjusted dynamically based on, for example, attributes of the input signals, the sound environment, or other factors. For example, referring to the arrangement of FIGS. 1A-1C, in one illustrative embodiment the sound processor 166 or the implant controller 135 is configured to evaluate/analyze received input signals to determine the primary or main sound "class" of the d signals (i.e., determine the environment in which the cochlear implant 100 is currently/presently located). That is, the sound processor 166 or the implant controller 135 is configured to use the received sound signals to "classify" the ambient sound environment of the cochlear implant 100 and/or the sound signals into one or more sound categories (i.e., determine the input signal type). The sound classes/categories may include, but are not limited to, "Speech," "Noise," "Speech+Noise," "Music," and "Quiet." Using the determined class, the implant controller 135 is configured to dynamically adapt the interleaving parameters.

As noted elsewhere herein, electrical feedback path(s) between an output channel and an input channel may be the result of any of a number of one or more different causes (e.g., via the recipient's tissue/fluid, fluid ingress into encapsulation of the device, etc.). However, it is also possible for implantable input and output channels to exist without the presence of electrical feedback path(s) there between. As such, in certain embodiments, the interleaving techniques presented herein may only be activated after the detection of electrical feedback at an input channel. For example, again referring to the example of FIGS. 1A-1C, the implant controller 135 or other element of cochlear implant 100 may be configured to monitor (e.g., periodically) the input channels 156(1) and 156(2) for potential electrical feedback. The electrical feedback from an output channel 158(1)-158(24) creates interference that, in certain examples, may be identified as predetermined/known noise patterns in the input channel. Therefore, in certain embodiments, the cochlear implant 100 (e.g., implant controller 135) is configured to monitor (e.g., periodically) the input channels 156(1) and 156(2) for noise that is likely attributable to (i.e., the result of) electrical feedback from one or more of the output channels 158(1)-158(24).

In other embodiments, the implant controller 135 may be configured to periodically (e.g., such as once per day, once per week, etc.) initiate an electrical feedback evaluation process to determine whether electrical feedback is present between any of the output-to-input channel combinations. In these embodiments, the implant controller 135 can evaluate (e.g., sequentially) each of the forty-eight output-to-input channel combinations to determine whether electrical feedback is present.

Once the implant controller 135 determines that electrical feedback is likely present at one or more of the input channels 156(1) or 156(2), the cochlear implant 100 can initiate sampling and stimulation interleaving operations, as described above. Using these monitoring mechanisms, the implant controller 135 may also be configured to automatically initiate dynamically adaptions to the interleaving parameters, also as described above.

Figure 7:
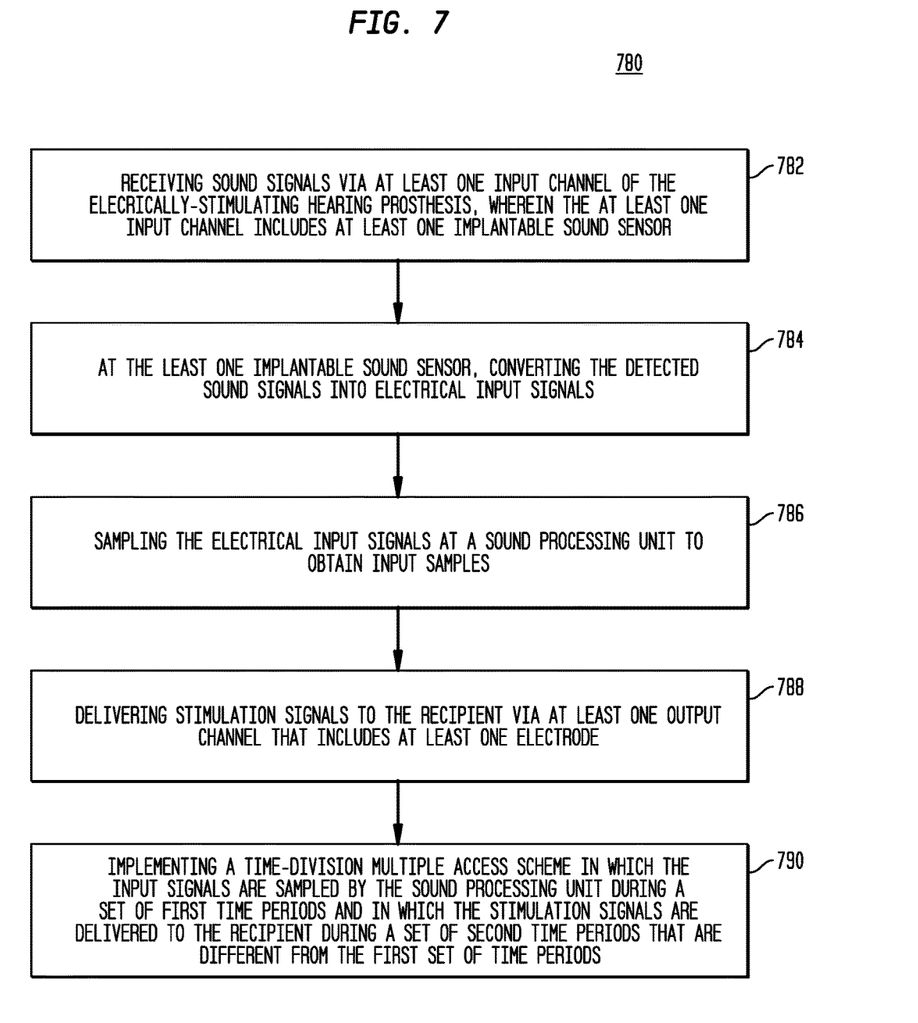
FIG. 7 is a flowchart of a method in accordance with certain embodiments presented herein.

FIG. 7 is a flowchart of a method 780 performed at an electrically-stimulating hearing prosthesis, in accordance with embodiments presented herein. Method 780 begins at 782 where sound signals are received via at least one input channel of the electrically-stimulating hearing prosthesis. The at least one input channel includes at least one implantable sound sensor. At 784, the least one implantable sound sensor converts the detected sound signals into electrical input signals. At 786, the sound processing unit samples the electrical input signals to obtain input samples and, at 788, stimulation signals are delivered to the recipient via at least one output channel that includes at least one electrode. At 790, a time-division multiple access scheme is implemented in which the input signals are sampled by the sound processing unit only during a set of first time periods and in which the stimulation signals are only delivered to the recipient during a set of second time periods that are different from the first set of time periods.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A totally implantable electrically-stimulating hearing prosthesis configured to be disposed in a recipient, comprising:
    at least one input channel including an implantable sound sensor configured to convert received sound signals into electrical input signals; and
    a sound processing unit configured to sample the electrical input signals and to initiate generation of stimulation signals for delivery to the recipient via at least one output channel
    wherein the sound processing unit is configured to synchronize sampling of the input signals and the delivery of the stimulation signals to the recipient so that the sampling is performed outside of a selected temporal proximity to the delivery of the stimulation signals.

2. The totally implantable electrically-stimulating hearing prosthesis of claim 1, wherein the sound processing unit is configured to execute a time interleaving scheme in which the sampling of the electrical input signals occurs only in a set of first time periods and the delivery of stimulation signals to the recipient occurs only in a set of second time periods that are interleaved with the set of first time periods in a successive and alternating pattern.

3. The totally implantable electrically-stimulating hearing prosthesis of claim 2, wherein the first and second sets of time periods are non-overlapping.

4. The totally implantable electrically-stimulating hearing prosthesis of claim 1, wherein the sound processing unit samples the input signals between time periods in which the stimulation signals are delivered to the recipient.

5. The totally implantable electrically-stimulating hearing prosthesis of claim 1, further comprising:
    an implant controller configured to detect the presence of one or more electrical feedback paths between the at least one output channel and the at least one input channel, wherein the one or more electrical feedback paths enable electrical feedback, which comprises a portion of stimulation signals on the output channel, to appear in the input channel,
    wherein the sound processing unit is configured to synchronize sampling of the electrical input signals and the delivery of the stimulation signals only after the implant controller detects the presence of one or more electrical feedback paths.

6. The totally implantable electrically-stimulating hearing prosthesis of claim 5, wherein to detect the presence of one or more electrical feedback paths between the at least one output channel and the at least one input channel, the implant controller is configured to:
    monitor the at least one input channel for noise that is likely attributable to electrical feedback from the output channel.

7. The totally implantable electrically-stimulating hearing prosthesis of claim 5, wherein to detect the presence of one or more electrical feedback paths between the at least one output channel and the at least one input channel, the implant controller is configured to:
    monitor the at least one input channel for the presence of one or more predetermined noise patterns.

8. The totally implantable electrically-stimulating hearing prosthesis of claim 1, wherein synchronizing the sampling of the input signals and the delivery of the stimulation signals results in the omission of incoming sound information, wherein the sound processing unit is configured to interpolate between input samples to estimate missing incoming sound information and to initiate generation of stimulation signals for delivery to the recipient based, at least in part, on the estimates of the missing incoming sound information.

9. The totally implantable electrically-stimulating hearing prosthesis of claim 1, wherein synchronizing the sampling of the input signals and the delivery of the stimulation signals results in the omission of incoming sound information, wherein the sound processing unit is configured to initiate generation of stimulation signals for delivery to the recipient by duplicating one or more input samples in place of omitted incoming sound information.

10. The totally implantable electrically-stimulating hearing prosthesis of claim 1, wherein the implantable sound sensor comprises an implantable microphone.

11. A totally implantable electrically-stimulating hearing prosthesis configured to be disposed in a recipient, comprising:
    at least one output channel terminating in an implantable electrode;
    at least one input channel comprising an implantable sound sensor configured to convert received sounds into input signals; and
    a sound processing unit configured to sample the input signals and to initiate generation of stimulation signals for delivery to the recipient,
    wherein the sound processing unit executes a time interleaving scheme in which the sound processing unit samples the input signals during a set of first time periods and in which the stimulation signals are delivered to the recipient during a set of second time periods, wherein the second time periods are interleaved with the first time periods in a successive and alternating pattern.

12. The totally implantable electrically-stimulating hearing prosthesis of claim 11, wherein the sound processing unit is configured to obtain a plurality of samples in each of the first time periods.

13. The totally implantable electrically-stimulating hearing prosthesis of claim 11, further comprising a stimulator unit configured to generate the stimulation signals for delivery to the recipient, wherein the stimulator unit is configured to generate and deliver a plurality of stimulation signals in each of the second time periods.

14. The totally implantable electrically-stimulating hearing prosthesis of claim 11, wherein the first and second sets of time periods are non-overlapping.

15. The totally implantable electrically-stimulating hearing prosthesis of claim 11, wherein the first time periods and the second time periods have a same time length.

16. The totally implantable electrically-stimulating hearing prosthesis of claim 11, wherein the first time periods and the second time periods have different time lengths.

17. The totally implantable electrically-stimulating hearing prosthesis of claim 11, wherein a time length of each of the first time periods and the second time periods are recipient-specific and determined during a fitting session.

18. The totally implantable electrically-stimulating hearing prosthesis of claim 11, wherein a time length of the first time periods or the second time periods is dynamically adjustable based on one or more of an attribute of the received sounds or a sound environment of the totally implantable electrically-stimulating hearing prosthesis.

19. The totally implantable electrically-stimulating hearing prosthesis of claim 11, further comprising:
an implant controller configured to detect the presence of one or more electrical feedback paths between the at least one output channel and the at least one input channel, wherein the one or more electrical feedback paths enable electrical feedback, which comprises a portion of stimulation signals on the output channel, to appear in the input channel,
wherein the sound processing unit is configured to activate the time interleaving scheme only after the implant controller detects the presence of one or more electrical feedback paths.

20. The totally implantable electrically-stimulating hearing prosthesis of claim 19, wherein to detect the presence of one or more electrical feedback paths between the at least one output channel and the at least one input channel, the implant controller is configured to:
monitor the at least one input channel for noise that is likely attributable to electrical feedback from the output channel.

21. The totally implantable electrically-stimulating hearing prosthesis of claim 19, wherein to detect the presence of one or more electrical feedback paths between the at least one output channel and the at least one input channel, the implant controller is configured to:
monitor the input channel for the presence of one or more predetermined noise patterns.

22. A method performed at an electrically-stimulating hearing prosthesis, the method comprising:
receiving sound signals via at least one input channel of the electrically-stimulating hearing prosthesis, wherein the at least one input channel includes at least one implantable sound sensor;
at the least one implantable sound sensor, converting the sound signals into electrical input signals;
sampling the electrical input signals at a sound processing unit to obtain input samples;
delivering stimulation signals to the recipient via at least one output channel that includes at least one electrode; and
implementing a time-division multiple access scheme in which the input signals are sampled by the sound processing unit during a set of first time periods and in which the stimulation signals are delivered to the recipient during a set of second time periods that are different from the first set of time periods.

23. The method of claim 22, wherein implementing a time-division multiple access scheme comprises:
time interleaving the sets of first and second time periods in a successive and alternating pattern.

24. The method of claim 22, further comprising:
obtaining a plurality of input samples during each of the first time periods.

25. The method of claim 22, further comprising:
delivering a plurality of stimulation signals in each of the second time periods.

26. The method of claim 22, wherein the first and second sets of time periods are non-overlapping.

27. The method of claim 22, wherein the first time periods and the second time periods have a same time length.

28. The method of claim 22, wherein the first time periods and the second time periods have different time lengths.

29. The method of claim 22, wherein a time length of each of the first time periods and the second time periods are recipient-specific and determined during a fitting session.

30. The method of claim 22, further comprising:
dynamically adjusting a time length of one or more of the first time periods or the second time periods based on one or more of attributes of the sound signals and a sound environment of the electrically-stimulating hearing prosthesis.

31. The method of claim 22, further comprising:
detecting the presence of one or more electrical feedback paths between the at least one output channel and the at least one input channel, wherein the one or more electrical feedback paths enable electrical feedback, which comprises a portion of stimulation signals on the output channel, to appear in the input channel,
wherein the time-division multiple access scheme is activated only after detection of the presence of one or more electrical feedback paths.

32. The method of claim 22, wherein detecting the presence of one or more electrical feedback paths between the at least one output channel and the at least one input channel comprises:
monitoring the at least one input channel for noise that is likely attributable to electrical feedback from the output channel.

33. The method of claim 22, wherein detecting the presence of one or more electrical feedback paths between the at least one output channel and the at least one input channel comprises:
monitoring the input channel for the presence of one or more predetermined noise patterns.

* * * * *